(12) United States Patent
DJang

(10) Patent No.: US 6,713,094 B2
(45) Date of Patent: Mar. 30, 2004

(54) METHOD FOR INHIBITING PATHOGENESIS ASSOCIATED WITH PARTICLE-INHALATION

(75) Inventor: Arthur DJang, Jamestown, NY (US)

(73) Assignee: Santé International, Inc., Jamestown, NY (US)

(*) Notice: Subject to any disclaimer, the term of this patent is extended or adjusted under 35 U.S.C. 154(b) by 14 days.

(21) Appl. No.: 10/233,711

(22) Filed: Sep. 3, 2002

(65) Prior Publication Data

US 2003/0157203 A1 Aug. 21, 2003

Related U.S. Application Data

(60) Provisional application No. 60/357,601, filed on Feb. 15, 2002.

(51) Int. Cl.⁷ ............................................... A61K 35/78
(52) U.S. Cl. ........................ 424/729; 424/725; 424/765; 424/777
(58) Field of Search ................................ 424/729, 725, 424/765, 777

(56) References Cited

U.S. PATENT DOCUMENTS

| 5,910,308 A | 6/1999 | DJang | .......................... 424/724 |
| 6,168,795 B1 | 1/2001 | DJang | .......................... 424/729 |

*Primary Examiner*—Herbert J. Lilling
(74) *Attorney, Agent, or Firm*—M. Bud Nelson

(57) ABSTRACT

Provided is a method for therapy of a pulmonary disease, the method comprising administering to an individual a composition in an amount effective to inhibit pulmonary inflammation, wherein the composition comprises an extract of *Gynostemma pentaphyllum*, an extract of *Crataegus pinnatifida*, and an extract of *Camellia sinensis*.

20 Claims, 2 Drawing Sheets

METHOD FOR INHIBITING PATHOGENESIS ASSOCIATED WITH PARTICLE-INHALATION

This is a nonprovisional application based on earlier co-pending provisonal application, application No. 60/357,601 filed Feb. 15, 2002, the disclosure of which is herein incorporated by reference.

FIELD OF THE INVENTION

The present invention relates to a method of using an herbal extract-based composition to inhibit pathogenesis induced by inhalation of particles. More particularly, provided is a method of therapy for (to treat and/or prevent) pulmonary disease (acute and/or chronic) in an individual, wherein administered to the individual is a composition in an amount effective to reduce inflammation; and wherein the composition comprises an extract of *Gynostemma pentaphyllum*, an extract of *Crataegus pinnatifida*, and an extract of *Camellia sinensis*.

BACKGROUND OF THE INVENTION

Inhalation of inorganic (e.g., mineral) dust is known to induce pathological changes in lung tissue leading to pulmonary disease. Inorganic dust may include, but is not limited to silica, asbestos, cristobalite, man-made vitreous fibers, and the like. For example, inhalation of silica (e.g., silcon dioxide, quartz) can cause inflammation, pulmonary fibrosis, and lead to respiratory impairment. Inhalation of crystalline silica is known to be associated with both acute and chronic pulmonary disease. Injury to the lung comprising pulmonary disease may result from one or more of the following mechanisms: (a) silica-induced release of lysosomal enzymes from alveolar macrophages; (b) silica-induced activation and release of reactive oxygen intermediates (e.g., one or more of superoxide anion radical, hydrogen peroxide, hydroxyl radical, nitric oxide, and the like) from alveolar macrophages which may result in oxidant-induced damage to lung tissue (e.g., parenchyma); and (c) silica-induced release of mediators from alveolar macrophages which enhance the proliferation of fibroblasts and other processes which can promote fibrosis.

Various forms of asbestos, such as chrysotile, crocidolite and amosite, have been found to be toxic to mammals, particularly when inhaled. Inhalation of asbestos can induce one or more of inflammation and pulmonary fibrosis, either or both of which can lead to pulmonary disease such as respiratory impairment, as well as promote development of malignant pleural mesotheliomas. It is believed that inhalation of asbestos can induce pulmonary disease utilizing similar or same mechanisms as inhalation of silica. For example, inhaled asbestos (e.g., crystalline particles and/or fibers) typically contacts pulmonary macrophages which induces an inflammatory response characterized by production and release of toxic, reactive oxygen intermediates in the lung. Additionally, in vivo and in vitro studies show that alveolar macrophages, following exposure to asbestos, can release neutrophil chemotaxins such as interleukin-8 which can further contribute to inflammation in the respiratory tract.

Additional concerns for inhalation exposure to harmful inorganic dust have been raised by the collapse of the World Trade Center and the smoke from the associated fires. The steel columns of the World Trade Center were coated with sprayed asbestos as a fire retardant. Upon the collapse of the buildings, a fine white dust could be seen, the dust including pulverized concrete, tons of fine particles of asbestos and other inorganic dust such as particles containing one or more of silicon, sulfur, titanium, vanadium, and nickel. Some reports estimate that, as a result of the collapse, nearly 5,000 tons of asbestos were released in Manhattan. Those people in the vicinity of the collapsed buildings (including, but not limited to, firefighters, other rescue workers, public safety workers, construction workers, office workers, students, residents, and the like) have been and may continue to be exposed to such inorganic dusts. Not only is dust released during the ongoing clean-up of Ground Zero, but homes and offices contain dust in the carpets, drapery, and other furnishings. Pulmonary diseases, likely both acute and chronic, have been attributed to the inhalation of dusts such as pulverized concrete, fiberglass, asbestos, and other particulates that filled the air following the collapse of the towers, as well as the fires that burned thereafter. Symptoms include chest tightness, bloody noses, sinus infections, and other respiratory ailments, including what is now termed as the "World Trade Center cough" (a persistent cough resulting from pulmonary inflammation). Nearly 1 in 4 firefighters who have been working at the Ground Zero site complain of having the World Trade Center cough, and a heaviness in their chest that is "like a bad cold that doesn't clear up". Of these firefighters, at least 10% have positive CAT scans showing pulmonary inflammation as a result of their exposure. Evaluations of the area by leading asbestos researchers show the increased risk to people who live, work, or study in the area could be as high as one additional cancer death for every 10 people exposed. It has been reported (e.g., by EPA experts, and CDC physicians) that even a one time dose of asbestos, if large enough, can raise the risk of mesothelioma. In addition to the acute respiratory illnesses that people are experiencing, it is now clear, as time progresses, that some individuals are experiencing chronic pulmonary disease as a result of the World Trade Center collapse. The chronic pulmonary disease may include, but is not limited to, one or more of chronic infectious sinus conditions, chronic coughing, wheezing, asthma, and a disorder known as "reactive airways dysfunction syndrome". Of those with chronic symptoms, more than 15% of the individuals tested have the presence of nodules and granulomas in their lungs—classic signs of disease caused by inhalation of inorganic dusts.

Additionally, pulmonary disease comprising bronchiolitis obliterans is a disease initiated by inhalation of particles (inorganic dust, organic dust, and a combination thereof) in the small conducting airways of the respiratory tract, and which leads to inflammation of these airways that can ultimately result in irreversible airway obstruction. Examples of occupations that can develop such bronchiolitis through the inhalation of particles includes silo workers, textile workers, and workers in the food industry (food-flavoring, microwave popcorn packaging, and the like).

Hence, there is a need for a method for inhibiting pathogenesis induced by inhalation of particles (inorganic dust, organic dust, or a combination thereof) by an individual. More particularly, there is a need for a method of therapy to treat or prevent pulmonary disease (including respiratory ailments) in an individual, wherein administered to the individual is a composition in an amount effective to reduce inflammation induced by inhalation of inorganic dust in the respiratory tract, particularly in the lungs. By inhibiting such inflammation, inherently reduced is any subsequent sequelae such as fibrosis, granulomata, and/or other pathological changes that may lead to development and/or progression of pleural mesothelioma.

SUMMARY OF THE INVENTION

The invention relates to a method for inhibiting pulmonary disease in, by inhibiting inflammation in the respiratory tract of, an individual. In one embodiment, administered to an individual whom has inhaled particles (comprising inorganic dust, organic dust, or a combination thereof) is a composition in an amount effective to reduce inflammation induced in the respiratory tract of the individual as a result of the inhaled particles.

In another embodiment of the present invention, the method for inhibiting pulmonary disease comprises administering, to an individual at risk for inhaling particles (e.g., due to occupation or environmental exposure), the composition in an amount to be effective prophylactically; i.e., so that the active ingredients of the composition are already present in the respiratory tract of the individual so as to reduce inflammation upon the inhalation of the particles.

The composition, and methods of making the composition are disclosed in U.S. Pat. No. 5,910,308; and methods for using the composition in anticancer therapy are disclosed in U.S. Pat. No. 6,168,795 (the disclosures of which are herein incorporated by reference). The composition comprises about 10 to about 30 percent by weight of *Gynostemma pentaphyllum* extract, about 10 to about 30 percent by weight of green tea extract, and about 40 to about 75 percent by weight of hawthorn berries extract. The preferred composition comprises about 10 to about 30 percent by weight of a mixture of an aqueous extract and an alcohol extract of *Gynostemma pentaphyllum*, about 10 to about 30 percent by weight of a mixture of an aqueous extract and an alcohol extract of *Camellia sinensis* (green tea), and about 40 to about 75 percent by weight of a mixture of an aqueous extract and an alcohol extract of *Crataegus pinnatifida* (hawthorn leaves and/or berries). *Gynostemma pentaphyllum*, also known as 5-leaf ginseng or Jiaogulan or southern ginseng, is from the cucumber family and is rich in special saponins termed "gypenosides" which are similar, and some identical, to the ginsenosides found in ginseng, but at a level several fold higher. The leaves and berries of *Crataegus pinnatifida*, also known as hawthorn, contain saponins, flavonoids (including hyperoside), and anthocyanins (including proanthocyanidins). Leaves from the *Camellia sinensis* plant, particularly when processed into green tea, contain polyphenols including catechins such as epigallocatechin-3 gallate (ECGC), epigallocatechin, and epicatechin-3-gallate. While *Gynostemma pentaphyllum*, *Crataegus pinnatifida*, and *Camellia sinensis* have been used individually for health promoting and therapeutic purposes, not described is the ability of a composition comprising an extract of *Gynostemma pentaphyllum*, an extract of *Crataegus pinnatifida* (hawthorn) and an extract of *Camellia sinensis* (green tea) to neutralize oxidative damages induced by the interaction between inhaled particles and alveolar macrophages.

The above and other objects, features, and advantages of the present invention will be apparent in the following Detailed Description of the Invention when read in conjunction with the accompanying drawings and embodiments.

DETAILED DESCRIPTION OF THE INVENTION

Definitions

Figure 1A:
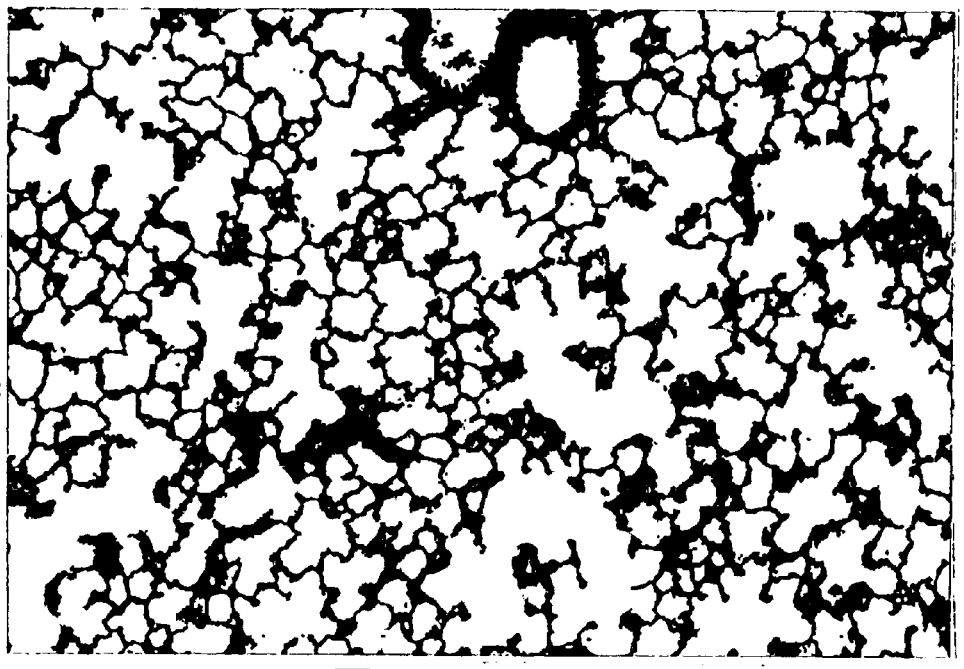
FIG. 1A is a photograph of a histochemical staining of a lung tissue section of a rat not exposed to asbestos particle inhalation.

The terms "pulmonary disease" and "pathogenesis induced by inhalation of particles" are used interchangeably herein, for purposes of the specification and claims, to mean one or more of pulmonary inflammation, World Trade Center cough, alveolitis, bronchiolitis, asbestosis, silicosis, coal miner's pneumoconiosis, granulomatous inflammation of the lungs, and inflammation underlying development and/or progression of pleural mesothelioma, and in a preferred embodiment, also including pleural mesothelioma itself (originating from pluripotential mesothelial cells rather than of ductal epithelial cell origin).

The term "inflammation" is used herein, for purposes of the specification and claims, to mean one or more of acute inflammation, chronic inflammation, diffuse inflammation, specific inflammation, toxic inflammation, reactive inflammation, interstitial inflammation, and focal inflammation. In a preferred embodiment, "inflammation" is meant to include involvement of one or more types of immune cells (e.g., neutrophils, leukocytes, macrophages, etc.) which directly and/or indirectly mediates an inflammatory process, and more preferably, an inflammatory process mediated by the involvement of alveolar macrophages with inhaled particles.

The term "individual" is used herein, for purposes of the specification and claims, to mean an animal, preferably a mammal, and more preferably, a human.

The terms "particles" or inhaled particles" are used interchangeably, for purposes of the specification and claims, to mean organic particulate matter (e.g., organic dust as known in the art), inorganic particulate matter (e.g., inorganic dust), or a combination thereof, the particulate matter capable of being inhaled by an individual, and capable of inducing inflammation once inhaled by the individual. Inorganic particulate matter is well known in the art to include, but is not limited to, pulverized concrete, fiberglass, asbestos, silica, cristobalite, man-made vitreous fibers, and a combination thereof.

Models for Human Disease

In some of the following embodiments used to illustrate the methods of the present invention, it is important to consider the following concepts. In vitro experiments involving the interaction between particles (inorganic dust, organic dust or a combination thereof) and alveolar macrophages have been accepted by those skilled in the art for modeling human pulmonary disease induced by inhalation of particles for the following reasons. The primary mediators of pulmonary inflammation as a result of inhalation of particles of inorganic dust and/or organic dust are alveolar macrophages. For example, both in vitro and in vivo: (a) alveolar macrophages come in contact with particles of inorganic dust, and then engulf the particles; and (b) as a result of the interaction with particles of inorganic dust, alveolar macrophages release mediators of inflammation such as (i) cytotoxic enzymes, (ii) reactive oxygen intermediates, and (iii) mediators (e.g., cytokines and the like) which enhance the proliferation of fibroblasts and other processes which can promote fibrosis. In vivo, the release of cytotoxic enzymes and reactive oxygen intermediates causes lipid peroxidation of cell membranes, as well as DNA damage, cell death and tissue damage. For example, upon engulfing particles of inorganic dust, alveolar macrophages enter the lymphatics and interstitial tissue where they release mediators of inflammation. The process is repeated because when macrophages die in the interstitial tissue, the particles of inorganic dust are released and then engulfed by other macrophages. Repeating of this process leads to formation of nodules and fibrosis, which can ultimately lead to functional impairment such as reduction of lung volumes and respiratory insufficiency. A similar process has been observed with continuous or frequent exposure (such as by occupational exposure) to organic dust.

Such processes have also been observed in animal models (e.g., rat or sheep) in modeling the pathological changes seen in humans who have inhaled inorganic dust. For example, in a rat model of asbestos exposure, inhaled asbestos fibers deposit in the alveoli, followed by accumulation of alveolar macrophages at the sites of inhaled dust, and subsequent release of inflammatory mediators by the alveolar macrophages (see, e.g., Schapira et al., 1991, *Exp. Lung Res.* 17:1011–24). As observed in both rats and humans, following exposure to inorganic dusts, there is decreased activity of antioxidation enzymes (e.g., superoxide dismutase ("SOD"), glutathione peroxidase ("GSH-Px") and the like). Likewise, the cytotoxic effect of inorganic dust (e.g., quartz) observed in in vitro and in vivo studies model the cytotoxic effects of quartz inhalation in humans (see, e.g., Larivee et al., 1990, *Lung*, 168:151–158; for correlation between asbestos-induced disease in humans and in vitro studies using rabbit alveolar macrophages, see, e.g., Jaurand et al., 1977, *Environ. Res.* 2:245–54). A physiological basis for scaling up therapeutic agents from animal models to humans is known to those skilled in the art.

The method according to the present invention for inhibiting pulmonary disease by administering a composition in an effective amount to inhibit inflammation may be more apparent by the following examples which are provided for purposes of illustration, and not limitation.

EXAMPLE 1

In vitro and in vivo, engulfment of particles comprising inorganic dust particles by alveolar macrophages subsequently causes DNA damage in the alveolar macrophages. Also illustrated in this example is a method for inhibiting inflammation by contacting alveolar macrophages with the composition described herein in an effective amount to inhibit inflammation. In this embodiment, illustrated is the efficacy of inhibiting pulmonary disease, by inhibiting a process of inflammation as measured by a reduction in DNA damage induced by inorganic dust, in the presence of the composition comprising the combination of herbal extracts as previously described herein in more detail (also known as ONCOLYN®). Alveolar macrophages were isolated from rat lungs by bronchoalveolar lavage and then collected by centrifugation using standard methods known in the art. The alveolar macrophages were further purified by incubating the collected cells on a plastic surface, and removing the non-adherent cells. The viability of the adherent alveolar macrophages was estimated by Trypan blue dye exclusion to be at least 99%. Alveolar macrophages, at a concentration of $2\times10^6$ cells/ml in tissue culture medium (RPMI with 10% serum supplement), were incubated alone ("control") or with 50 µg/ml of inorganic dust (either silica or asbestos, particle size of 5 µm), or in the presence of the inorganic dust and Oncolyn (the latter at a concentration ranging from 25 µg/ml to 200 µg/ml) for 18 hours under standard conditions of cell culture. The alveolar macrophages were then collected to assess DNA strand breakage by single cell gel electrophoresis, also known as a "comet assay" because a DNA-damaged cell, when electrophoresed and stained with ethidium bromide, resembles a comet (the cell) with a "trail" of fluorescing broken DNA strands. The assay was performed using methods standard in the art. Briefly, the cultured alveolar macrophages were collected, mixed with 1% low-melting temperature agarose, and then placed on microscope slides already containing a surface covered with a thin layer of 0.5% agarose. The slides were then stored at 4° C. to allow for solidification of the agarose. The slides were then immersed in a detergent-containing lysing buffer at 4° C. for 1 hour. The slides were then placed in a horizontal electrophoresis unit containing electrophoresis buffer, and electrophoresed for 20 minutes at 25V and 300 mA. Following electrophoresis, the slides were washed with buffer, stained with ethidium bromide (25 µg/ml), coverslipped and incubated in a humidity chamber at 4° C. DNA strand breakage was determined by microscopic visualization of the percentage of comet cells observed, and the length of migration of broken DNA from the cells ("migration length" expressed in µm). The results are shown in Tables 1 (for silica) and 2 (for asbestos). As shown in Table 1, there is a statistically significant reduction in DNA damage (as measured by the percent comet cells detected) in alveolar macrophages treated with silica and all concentrations of the composition tested versus silica alone. As shown in Table 2, there is a statistically significant reduction in DNA damage (as measured by the percent comet cells detected, and migration distance) in alveolar macrophages treated with asbestos and all concentrations of the composition tested versus asbestos alone.

TABLE 1

DNA damage of alveolar macrophages

| Cell Culture contents | Cells Counted | % comet cells | Migration distance |
|---|---|---|---|
| control | 71 | 2.8 | 12 ± 0 |
| +silica | 69 | 56.5 | 58 ± 2 |
| +silica + Oncolyn (25 µg/ml) | 78 | 32.8 | 52 ± 2 |
| +silica + Oncolyn (50 µg/ml) | 83 | 27.7 | 47 ± 4 |
| +silica + Oncolyn (75 µg/ml) | 105 | 14.3 | 42 ± 2 |
| +silica + Oncolyn (100 µg/ml) | 67 | 19.4 | 50 ± 2 |
| +silica + Oncolyn (200 µg/ml) | 78 | 26.9 | 51 ± 1 |

TABLE 2

DNA damage of alveolar macrophages

| Cell Culture contents | Cells counted | % comet cells | migration distance |
|---|---|---|---|
| control | 78 | 5.1 | 18 ± 2 |
| +asbestos | 75 | 62.7 | 60 ± 3 |
| +asbestos + Oncolyn (50 µg/ml) | 67 | 46.2 | 38 ± 7 |
| +asbestos + Oncolyn (75 µg/ml) | 131 | 30.0 | 36 ± 7 |
| +asbestos + Oncolyn (100 µg/ml) | 69 | 43.5 | 49 ± 10 |

Taken together, the results shown in Table 1 and Table 2 are evidence of inhibition of inflammation as measured by the inhibition of DNA damage in alveolar macrophages induced by exposure to particles comprising inorganic dust.

EXAMPLE 2

In vitro and in vivo, engulfment of particles such as inorganic dust particles by alveolar macrophages subsequently causes a decrease in activity of antioxidation enzymes from alveolar macrophages. In this embodiment, illustrated is the efficacy of inhibiting pulmonary disease, by inhibiting a process of inflammation as measured by antioxidation enzyme activity induced by inorganic dust in the presence or absence of the composition (Oncolyn). Also illustrated in this example is a method for inhibiting inflammation by contacting alveolar macrophages with the composition described herein in an effective amount to inhibit inflammation. Alveolar macrophages were isolated and purified as previously described in Example 1 herein. The alveolar macrophages were then cultured alone, in the presence of inorganic dust, or in the presence of inorganic dust and various concentrations of the composition, as described in Example 1. Supernatants were collected from the respective cultures and assayed for units of activity of antioxidation enzymes superoxide dismutase (SOD) and glutathione peroxidase (GSH-Px) using commercial kits and methods standard in the art. The results (the average of six experiments) are shown in Tables 3 (for silica) and 4 (for asbestos). As shown in Table 3, there is a statistically significant increase in activity of antioxidation enzymes in alveolar macrophages treated with silica and all concentrations of the composition tested versus silica alone. As shown in Table 4, there is a statistically significant increase in activity of antioxidation enzymes in alveolar macrophages treated with asbestos and all concentrations of the composition tested versus asbestos alone.

TABLE 3

Activity of antioxidation enzymes of alveolar macrophages

| Cell Culture contents | SOD | GSH-Px |
|---|---|---|
| Control | 32 ± 1 | 0.39 ± 0.06 |
| +silica | 24 ± 3 | 0.12 ± 0.02 |
| +silica + Oncolyn (25 µg/ml) | 29 ± 1 | 0.13 ± 0.01 |
| +silica + Oncolyn (50 µg/ml) | 31 ± 2 | 0.20 ± 0.02 |
| +silica + Oncolyn (75 µg/ml) | 33 ± 2 | 0.19 ± 0.04 |
| +silica + Oncolyn (100 µg/ml) | 30 ± 2 | 0.19 ± 0.02 |
| +silica + Oncolyn (200 µg/ml) | 31 ± 2 | 0.17 ± 0.05 |

TABLE 4

Activity of antioxidation enzymes of alveolar macrophages

| Cell Culture contents | SOD | GSH-Px |
|---|---|---|
| control | 22 ± 2 | 0.29 ± 0.08 |
| +asbestos | 14 ± 3 | 0.16 ± 0.05 |
| +asbestos + Oncolyn (50 µg/ml) | 16 ± 3 | 0.30 ± 0.08 |
| +asbestos + Oncolyn (75 µg/ml) | 23 ± 2 | 0.30 ± 0.03 |
| +asbestos + Oncolyn (100 µg/ml) | 24 ± 2 | 0.31 ± 0.04 |

Taken together, the results shown in Table 3 and Table 4 are evidence of inhibition of inflammation as measured by the preservation (inhibition of a decrease) of antioxidation enzyme activity in alveolar macrophages exposed to inorganic dust.

EXAMPLE 3

In vitro and in vivo, engulfment of particles such as inorganic dust particles by alveolar macrophages subsequently causes a increase in reactive oxygen intermediates (e.g., free radicals) by alveolar macrophages. In this embodiment, illustrated is the efficacy of inhibiting pulmonary disease, by inhibiting a process of inflammation as measured by production of reactive oxygen intermediates induced by inorganic dust in the presence or absence of the composition (Oncolyn). Also illustrated in this example is a method for inhibiting inflammation by contacting alveolar macrophages with the composition described herein in an effective amount to inhibit inflammation. Alveolar macrophages were isolated and purified as previously described in Example 1 herein. The alveolar macrophages were then cultured alone, in the presence of inorganic dust, or in the presence of inorganic dust and various concentrations of the composition, as described in Example 1. Supernatants were collected from the respective cultures and assayed for unit concentration of nitric oxide (NO; $\mu M/2 \times 10^6$ cells) and activity of nitric oxide synthetase (NOS; U/ml) using commercial kits and methods standard in the art. The results (the average of six experiments) are shown in Tables 5 for silica. As shown in Table 5, there is a statistically significant decrease in reactive oxygen intermediates in the presence of alveolar macrophages treated with silica and all concentrations of the composition tested versus silica alone.

TABLE 5

Reactive oxygen intermediates

| Cell Culture contents | NO | NOS |
|---|---|---|
| Control | 0.038 ± 0.018 | 13.8 ± 1.7 |
| +silica | 0.094 ± 0.003 | 30.8 ± 3.4 |
| +silica + Oncolyn (25 µg/ml) | 0.069 ± 0.002 | 18.6 ± 2.5 |
| +silica + Oncolyn (50 µg/ml) | 0.058 ± 0.010 | 15.9 ± 1.4 |
| +silica + Oncolyn (75 µg/ml) | 0.054 ± 0.003 | 16.1 ± 4.2 |
| +silica + Oncolyn (100 µg/ml) | 0.054 ± 0.003 | 12.9 ± 2.3 |
| +silica + Oncolyn (200 µg/ml) | 0.066 ± 0.008 | 19.3 ± 2.2 |

The results shown in Table 5 are evidence of inhibition of inflammation as measured by the decrease of reactive oxygen intermediates in the presence of alveolar macrophages exposed to particles comprising inorganic dust. Thus, demonstrated herein is a method for inhibiting inflammation comprising contacting alveolar macrophages with the composition described herein in an effective amount to inhibit inflammation (as, for example, measured by one or more of a reduction in DNA damage, preservation of antioxidation enzyme activity, decrease of reactive oxygen intermediates, in alveolar macrophages treated according to the method of the present invention and exposed to particles as compared to alveolar macrophages exposed to particles only).

EXAMPLE 4

In this example, illustrated are embodiments of a method of according to the present invention for therapy of pulmonary disease. In a first embodiment, the method comprises administering to an individual the composition in an amount effective to inhibit inflammation induced by particles inhaled into the respiratory tract of the individual, wherein the composition preferably comprises about 10 to about 30 percent by weight of *Gynostemma pentaphyllum* extract, about 10 to about 30 percent by weight of green tea extract, and about 40 to about 75 percent by weight of hawthorn berries extract (as previously described herein in more detail). As known to those skilled in the art, an amount effective for therapy of pulmonary disease is an amount that can effect inhibition of pulmonary inflammation when administered to an individual who has pulmonary inflammation or is at risk of developing pulmonary inflammation. As known to those skilled in the art, the dosage and regimen comprising an amount effective to inhibit pulmonary inflammation may vary with the individual depending on such factors as the age, size, health, and metabolism of the individual; the type and/or amount of particles (e.g., organic dust, inorganic dust, or a combination thereof) which an individual inhales or is at risk of inhaling; the frequency of inhalation of the particles, the stage of any existing pulmonary disease; and related factors. An amount effective to inhibit pulmonary inflammation will generally comprise sufficient active ingredient to deliver from about 0.1 µg/kg to about 50 mg/kg (weight of active ingredient/body weight of individual). Preferably the composition will deliver at least 0.5 to 10 mg/kg, and more preferably at least 1 µg/kg to about 1 mg/kg.

The composition may be administered to an individual in any suitable systemic or local formulation, preferably in an amount effective to deliver a dosage which inhibits pulmonary inflammation in therapy of (e.g., inhibiting) pulmonary disease. The route of administration of the composition may be by any conventional route in which the composition can be safely and effectively delivered. Typically, compositions used for therapy can be administered by one or more routes including, but not limited to, intravenously, subcutaneously, orally, intra-tracheally, intramuscularly, intradermally, inhalation in suitable aerosol formulation, and the like. For oral administration, preferred forms of the composition include, but are not limited to, tablets, caplets, capsules, pills, lozenges, powders, suspensions, emulsions. The composition may further comprise a pharmaceutically acceptable carrier (e.g., one or more of aqueous fluid, liquid, water, saline, carbohydrate-containing solution, alcohol, oils, buffers or other physiological solution, gel, any well known biodegradable and biocompatible carrier, one or more conventional excipients, one or more controlled release macromolecules (e.g., starch, cellulose, polyesters, binders, hydrogels, and the like), and the like). Typical ratios of active ingredients to ingredients other than the active ingredients present in a composition formulation are well known in the art.

Provided is a method of inhibiting pulmonary disease in an individual whom has inhaled particles capable of inducing pulmonary inflammation, the method comprising administering to the individual an amount of a composition effective to reduce pulmonary inflammation, wherein the composition comprises about 10 to about 30 percent by weight of a mixture of an aqueous extract and an alcohol extract of *Gynostemma pentaphyllum*, about 10 to about 30 percent by weight of a mixture of an aqueous extract and an alcohol extract of *Camellia sinensis*, and about 40 to about 75 percent by weight of a mixture of an aqueous extract and an alcohol extract of *Crataegus pinnatifida* (the "composition"). As an example of this method, a standard animal model of pulmonary disease was used. Wistar rats were divided into groups and anesthetized, wherein a "control" group received sterile saline administered intratracheally, and an "particle-exposed" group received saline suspensions of asbestos administered intratracheally. Some of the particle-exposed group of rats received orally 2.5 g/kg/day of the composition, whereas the remainder of the particle-exposed group did not receive any of the composition. Forty days after the rats were exposed to the particles: (a) lung tissue sections were obtained from rats of each group and stained for histochemical analysis; and (b) alveolar macrophages were isolated from all the rats of all of the groups using methods as described in Example 1 herein in more detail.

Figure 1B:
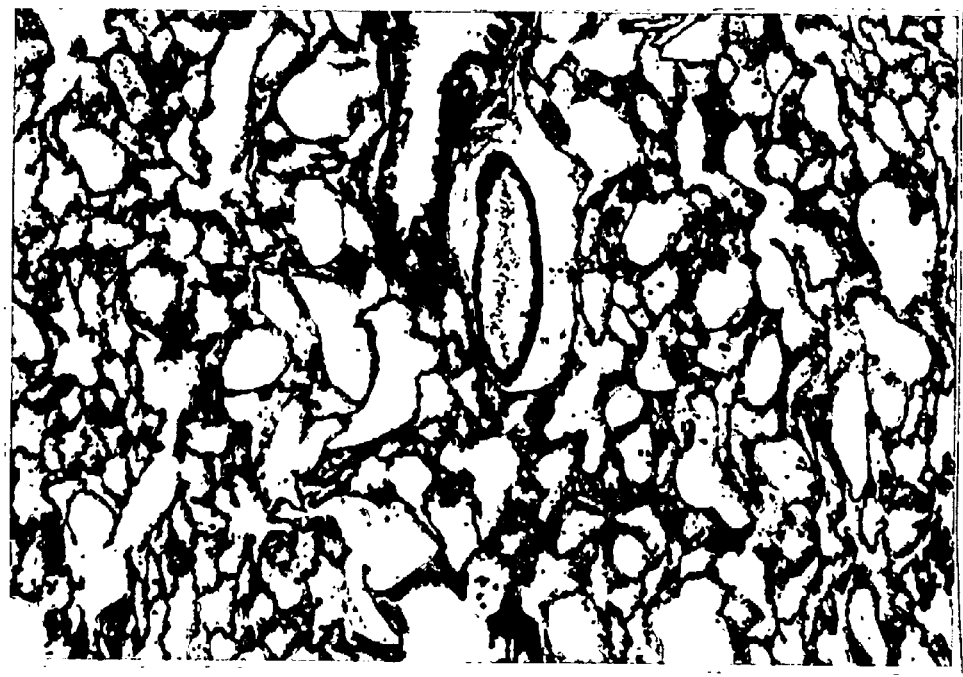
FIG. 1B is a photograph of a histochemical staining of a lung tissue section of a rat exposed to asbestos particle inhalation, and treated with the method according to the present invention.

Illustrated in FIG. 1A is the histochemical staining of a lung section from a rat of the control group. Illustrated in FIG. 1B is the histochemical staining of a lung tissue section of a rat exposed to asbestos particle inhalation, and treated with the method according to the present invention. Illustrated in FIG. 1C is the histochemical staining of a lung tissue section of a rat exposed to asbestos particle inhalation.

Figure 1C:
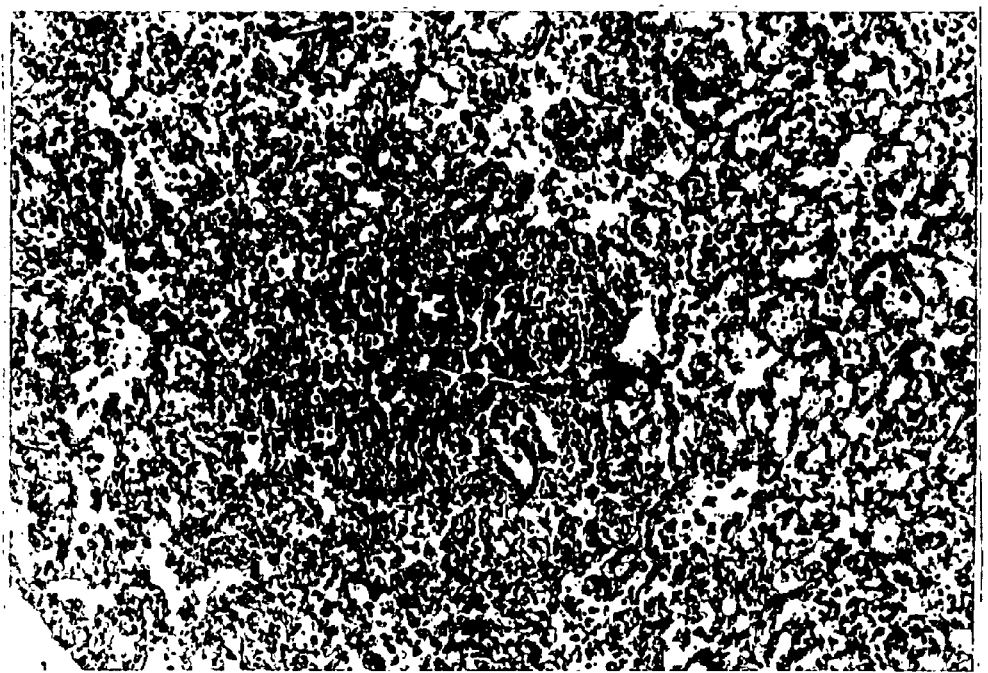
FIG. 1C is a photograph of a histochemical staining of a lung tissue section of a rat exposed to asbestos particle inhalation.

Note in FIG. 1C that the pathogenesis induced by asbestos inhalation is evident as acute and chronic bronchiolitis, and acute and chronic alveolitis with early confluent bronchopneumonia. In contrast to the pathology illustrated in FIG. 1C, and as shown in FIG. 1B, the lungs of rats exposed to asbestos and then treated according to the present invention show a resolving of mild inflammation evident as mild acute and chronic alveolitis. Thus, pulmonary disease is clearly inhibited by the method of the present invention.

DNA damage in the harvested alveolar macrophages was assessed using methods as described in more detail in Example 1 herein. Activity of antioxidation enzymes in the lung tissue of the rats was measured using methods described in Example 2 herein. The level of reactive oxygen intermediates was measured in the serum of the rats using methods described in Example 3 herein. As shown in Table 6, there is a statistically significant reduction in DNA damage (as measured by the percent comet cells detected, and migration distance) in alveolar macrophages of rats treated with particles and the composition tested versus particles alone. As shown in Table 7, treatment with the compound resulted in a preservation of antioxidation enzymes in the lung tissue of the particle-exposed and treated rats versus the particle-exposed rats. As shown in Table 8, treatment with the compound resulted in a decrease of reactive oxygen intermediates antioxidation enzymes in the serum of the particle-exposed and treated rats versus the particle-exposed rats.

TABLE 6

DNA damage of alveolar macrophages induced by in vivo particle exposure

| Administered Contents | Cells counted | % comet cells | Migration Distance |
| --- | --- | --- | --- |
| Control | 141 | 9.2 | 24 ± 1.6 |
| +asbestos | 133 | 63.2 | 51 ± 1.4 |
| +asbestos + Oncolyn | 181 | 29.3 | 33 ± 1.3 |

TABLE 7

Activity of antioxidation enzymes in lung tissue induced by in vivo particle exposure

| Administered Contents | SOD | GSH-Px |
| --- | --- | --- |
| Control | 38.8 ± 3.8 | 16.7 ± 3.7 |
| +asbestos | 19.9 ± 1.9 | 12.1 ± 1.4 |
| +asbestos + Oncolyn | 22.7 ± 1.9 | 14.8 ± 2.2 |

TABLE 8

Reactive oxygen intermediates in serum induced by in vivo particle exposure

| Administered Contents | NOS | NO |
| --- | --- | --- |
| Control | 8.5 ± 1.2 | 14.3 ± 1.8 |
| +asbestos | 11.4 ± 1.1 | 21.2 ± 3.4 |
| +asbestos + Oncolyn | 9.3 ± 1.0 | 9.6 ± 1.4 |

The results in Tables 6, 7, and 8 demonstrate that pulmonary disease in an individual, whom has inhaled particles capable of inducing pulmonary inflammation, can be inhibited by administering to the individual an amount of the composition effective to reduce pulmonary inflammation.

In another illustration of inhibiting pulmonary disease comprising pulmonary inflammation, and in this example, inflammation associated with the development and/or progression of mesothelioma, a 44 year old male having an occupation with high risk exposure to asbestos was diagnosed by imaging evaluation (CAT scans) and lung biopsies as having well differentiated, malignant pleural mesothelioma appearing as at least 6 masses and with inflammatory complications (pleural effusion, etc.). With no other treatment available, the individual was administered, by an oral route and in caplet form, 750 mg of the composition (Oncolyn), three times per day for four months. After four months, imaging evaluation of the individual showed an absence of pulmonary masses and absence of pleural effusions, i.e. the inflammation underlying the mesothelioma was inhibited and, additionally, the mesothelioma itself completely regressed to the point it was no longer detectable by CAT scans (in clinical remission). The method of therapy was continued, and inhibition of the pulmonary disease has remained (individual has remained free of pulmonary disease to date, approximately three years after the clinical diagnosis of mesothelioma with pneumonia and pleurisy (pulmonary inflammation)). The median survival time for malignant pleural mesotheliomas is approximately 7 months following first clinical symptoms (Merritt et al., 2001, *J. Surg. Oncol.* 78:171–4). No symptoms of toxicity or observed side effects in the individual were observed during therapy according to the method of the present invention.

From the foregoing, it will be obvious to those skilled in the art that various modifications in the above-described methods, and compositions can be made without departing from the spirit and scope of the invention. Accordingly, the invention may be embodied in other specific forms without departing from the spirit or essential characteristics thereof. Present embodiments and examples, therefore, are to be considered in all respects as illustrative and not restrictive, and all changes which come within the meaning and range of equivalency of the claims are therefore intended to be embraced therein.

What is claimed is:

1. A method of inhibiting pulmonary disease in an individual comprising administering to an individual an amount of a composition effective to inhibit pulmonary inflammation induced by particle inhalation, wherein the composition comprises about 10 to about 30 percent by weight of a mixture of an aqueous extract and an alcohol extract of *Gynostemma pentaphyllum*, about 10 to about 30 percent by weight of a mixture of an aqueous extract and an alcohol extract of *Camellia sinensis*, and about 40 to about 75 percent by weight of a mixture of an aqueous extract and an alcohol extract of *Crataegus pinnatifida*.

2. The method according to claim 1, wherein the pulmonary inflammation is induced by inhalation by the individual of inorganic dust.

3. The method according to claim 2, wherein the inorganic dust comprises silica.

4. The method according to claim 2, wherein the inorganic dust comprises asbestos.

5. The method according to claim 2, wherein the composition is administered to an individual at risk of inhaling inorganic dust.

6. The method according to claim 2, wherein the composition is administered to an individual who has inhaled inorganic dust.

7. The method according to claim 1, wherein the composition is administered orally to the individual.

8. The method according to claim 1, wherein the composition further comprises a pharmaceutically acceptable carrier.

9. The method according to claim 8, wherein the composition is administered orally to the individual.

10. A method of treating of an individual at risk of developing pulmonary disease an amount of a composition effective to inhibit pulmonary inflammation, wherein the composition comprises about 10 to about 30 percent by weight of a mixture of an aqueous extract and an alcohol extract of *Gynostemma pentaphyllum*, about 10 to about 30 percent by weight of a mixture of an aqueous extract and an alcohol extract of *Camellia sinensis*, and about 40 to about 75 percent by weight of a mixture of an aqueous extract and an alcohol extract of *Crataegus pinnatifida*.

11. The method according to claim 10, wherein the composition is administered orally to the individual.

12. The method according to claim 10, wherein the composition further comprises a pharmaceutically acceptable carrier.

13. The method according to claim 12, wherein the composition is administered orally to the individual.

14. A method of treating an individual who has inhaled inorganic dust, the method comprising administering to an individual an amount of a composition effective to inhibit pulmonary inflammation, wherein the composition comprises about 10 to about 30 percent by weight of a mixture of an aqueous extract and an alcohol extract of *Gynostemma pentaphyllum*, about 10 to about 30 percent by weight of a mixture of an aqueous extract and an alcohol extract of *Camellia sinensis*, and about 40 to about 75 percent by weight of a mixture of an aqueous extract and an alcohol extract of *Crataegus pinnatifida*.

15. The method according to claim 14, wherein the inorganic dust comprises silica.

16. The method according to claim 14, wherein the inorganic dust comprises asbestos.

17. The method according to claim 14, wherein the composition is administered orally to the individual.

18. The method according to claim 17, wherein the composition further comprises a pharmaceutically acceptable carrier.

19. The method according to claim 18, wherein the composition is administered orally to the individual.

20. A method of inhibiting inflammation, the method comprising contacting alveolar macrophages with an amount of a composition effective to inhibit inflammation measurable by inhibition of one or more of (a) DNA damage to the alveolar macrophages induced by contact of the alveolar macrophages with particles, (b) a decrease in antioxidation enzymes induced by contact of alveolar macrophages with particles, and (c) an increase in reactive oxygen intermediates induced by contact of alveolar macrophages with particles; wherein the composition comprises about 10 to about 30 percent by weight of a mixture of an aqueous extract and an alcohol extract of *Gynostemma pentaphyllum*, about 10 to about 30 percent by weight of a mixture of an aqueous extract and an alcohol extract of *Camellia sinensis*, and about 40 to about 75 percent by weight of a mixture of an aqueous extract and an alcohol extract of *Crataegus pinnatifida*.

* * * * *